United States Patent [19]

Willis et al.

[11] 4,351,955

[45] Sep. 28, 1982

[54] ALPHA-HYDROXYISOBUTYRIC ACID PROCESS

[75] Inventors: Carl L. Willis; Lynn H. Slaugh, both of Houston, Tex.

[73] Assignee: Shell Oil Company, Houston, Tex.

[21] Appl. No.: 204,676

[22] Filed: Nov. 5, 1980

[51] Int. Cl.$^3$ .............................................. C07C 59/00
[52] U.S. Cl. .................................. 562/579; 562/589; 260/513 R
[58] Field of Search .............................. 562/579, 589; 260/173 R

[56] References Cited

U.S. PATENT DOCUMENTS 2,229,897  1/1941  Migrdichian ........................ 562/579

FOREIGN PATENT DOCUMENTS 736518   6/1966  Canada ................................ 562/579
1468126  2/1971  Fed. Rep. of Germany ...... 562/589
1030727  5/1966  United Kingdom ................ 562/589

*Primary Examiner*—Paul J. Killos

[57] ABSTRACT

Acetone cyanohydrin is converted to alpha-hydroxyisobutyric acid by contacting the cyanohydrin with alpha-hydroxymethanesulfonic acid and water at a temperature of about 70°–125° C. The alpha-hydroxymethanesulfonic acid is an equilibrium product of the reaction of water, sulfur dioxide and formaldehyde.

5 Claims, No Drawings

ALPHA-HYDROXYISOBUTYRIC ACID PROCESS

FIELD OF THE INVENTION

This invention relates to a process of making alpha-hydroxyisobutyric acid from acetone cyanohydrin.

BACKGROUND OF THE INVENTION

Aliphatic monoprotic hydroxy acids, particularly alpha-hydroxyisobutyric acid, are well known for their applicability as eluents in cation exchange processes, particularly in the fractionation of lanthanide and actinide elements (J. Korkish, Modern Methods for the Separation of Metal Ions, Pergamon Press, Oxford (1969); G. R. Choppin & R. J. Silva, J. of Inorganic & Nuclear Chem., Vol. 3, p. 153 (1956)).

Alpha-hydroxyisobutyric acid is also as a precursor to methacrylic acid and related esters (see U.S. Pat. No. 2,101,821), compounds which are quite useful in the plastics industry.

SUMMARY OF THE INVENTION

Acetone cyanohydrin is converted to alpha-hydroxyisobutyric acid in high conversion and selectivity by contacting the cyanohydrin at a temperature of from about 75° C. to about 125° C. with an acid mixture prepared by reacting water, sulfur dioxide and formaldehyde. The by-product ammonium 2-hydroxymethane sulfonate is converted readily to ammonium bisulfite and formaldehyde by heating to greater than about 140° C., the formaldehyde produced being readily and economically recycled to the reaction mixture. Excess acid mixture is readily removed from the product reaction mixture by the application of heat and/or vacuum. The instant acid mixture is a more active hydrolysis agent than, for example, aqueous sulfuric acid and can much more readily be removed from the reaction product than other acids such as $H_2SO_4$.

DESCRIPTION OF THE PREFERRED EMBODIMENTS

The acetone cyanohydrin used as a starting material in the instant process is readily made from acetone and hydrogen cyanide by base-catalysed reaction. This chemistry is well-known and conventional.

The acid reaction mixture used to convert the cyanohydrin to the corresponding acid is prepared by reacting water, sulfur dioxide and formaldehyde to produce alpha-hydroxymethanesulfonic acid according to the following reaction.

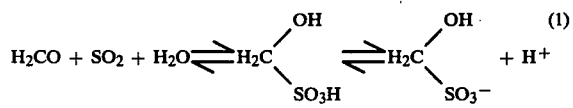

The resulting acid is a strong acid, at least as, if not stronger than hydrochloric acid. The above reaction is both temperature and pressure dependent with lower temperatures and higher pressures favoring the production of the sulfonic acid.

A unique feature of the instant acid is the easy reversibility of the acid formation according to equation (1). That is, when heated, sulfur dioxide is liberated and the solution becomes neutral. Decreasing the sulfur dioxide pressure for this system induces the same effect. The reversibility provides a method to remove unutilized acid from the reaction product. By increasing the temperature or lowering the pressure, the sulfur dioxide can be driven off leaving the carbonyl compound and water. The latter materials can then be removed by conventional means, such as distillation.

The reaction of the instant process proceeds as follows:

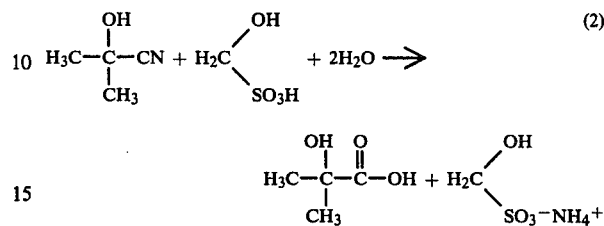

The by-product ammonium alpha-hydroxymethanesulfonate can readily be decomposed to formaldehyde and ammonium bisulfite by the application of heat, e.g.

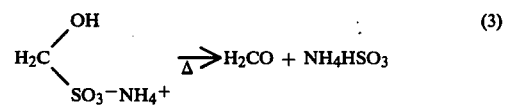

Temperatures of about 140° C. are required for this reaction and the formaldehyde can then be recycled to the starting reaction mixture.

As can be determined from equation (2), at least one mole of alpha-hydroxymethanesulfonic acid and 2 moles of water are needed for each mole of acetone cyanohydrin reacted. Preferably excess alpha-hydroxymethanesulfonic acid and water are utilized, say from about 1.5 to 7, more preferably from about 3 to 5 moles of alpha-hydroxymethanesulfonic acid per mole of acetone cyanohydrin reactant and about 5 to about 10 moles of water per mole of acetone cyanohydrin.

The alpha-hydroxymethanesulfonic acid may be prepared prior to reaction with the acetone cyanohydrin by reacting appropriate amounts of sulfur dioxide, water and formaldehyde, the latter two components conveniently being provided as an aqueous solution of formaldehyde. Alternatively, the sulfur dioxide, water and formaldehyde may be individually supplied to the reaction mixture, forming, in situ, the alpha-hydroxymethanesulfonic acid.

Reaction temperatures range from about 70° to about 125° C., preferably from about 75° to about 100° C. The reaction pressure is not critical and is conveniently one atmosphere or greater. After reaction, the alpha-hydroxyisobutyric acid is recovered from the reaction mixtures. The product acid may be readily esterified by reaction with an alcohol in the presence of an acid. The alpha-hydroxymethanesulfonic acid is also useful as a catalyst for esterification.

The process of this invention will be further described by the following illustrative embodiments which are provided for illustration and are not to be construed as limiting the invention.

In a typical preparation of alpha-hydroxymethanesulfonic acid, about 30 grams of $SO_2$ were condensed (dry ice/acetone bath) into a 200 cc Fisher-Porter pressure bottle. The reaction vessel was opened and slightly less than one equivalent of aqueous formaldehyde solution (37% w $H_2CO$) was added. The pressure bottle was sealed and the mixture warmed to room temperature.

The mixture was stirred vigorously overnight and then vented (SO$_2$) to atmospheric pressure. Analysis of the resulting aqueous phase (potentiometric titration with NaOH/H$_2$O) typically found about 5 M alpha-hydroxymethanesulfonic acid and a trace of SO$_2$. The solution was stored for up to four weeks in the pressure bottle without loss in acidity.

In a typical experiment about 28 grams of an approximately 5 M solution of alpha-hydroxymethanesulfonic acid were added to 8.5 grams of acetone cyanohydrin in a mechanically stirred round bottomed flask. The resulting solution was heated to the reaction temperature. Aliquots were removed from the reaction flask and analyzed directly. In addition, a portion of each aliquot was esterified (MeOH/H$_2$SO$_4$) and the concentration of methyl alpha-hydroxyisobutyrate determined.

Conversion was calculated according to the following.

$$\% \text{ Conversion} = \frac{[\text{cyanohydrin}]_{initial} - [\text{cyanohydrin}]_{product}}{[\text{cyanohydrin}]_{initial}} \times 100$$

The acetone cyanohydrin concentration was determined by potentiometric titration in i-propyl alcohol using 0.1 N NaOH/H$_2$O as the titrant. The nitrile was characterized by a unique break in the titration curve at high pH. A control experiment showed that the base was consumed with a 1:1 stoichiometry. For results in parentheses, the cyanohydrin concentration was determined by $^{13}$C NMR. When this technique was employed, the intensity of the singlet resonance at δ29 ppm ((CH$_3$)$_2$ C(OH) CN) was compared to that at δ27 ppm ((CH$_3$)$_2$ C(OH) CO$_2$H) and the nitrile concentration calculated directly from this ratio. The NMR technique does not account for starting material which may be converted to other products.

Selectivity was calculated according to the following.

$$\% \text{ Selectivity} = \frac{[\alpha\text{-hydroxy-i-butyric acid}]}{[\text{cyanohydrin}]_{initial} - [\text{cyanohydrin}]_{product}} \times 100$$

The α-hydroxy-i-butyric acid concentration was measured indirectly by esterification (MeOH/H$_2$SO$_4$) and analysis of the ester concentration by GLPC with an internal standard. A series of control experiments showed that this method gave values that were up to 15% lower than the actual acid concentration. For results in parentheses, the product acid concentration was determined by $^{13}$C NMR as outlined above.

The results of several representative experiments at 70° C. and 80° C. are shown below as Examples 1-4.

In Example 5, H$_2$SO$_4$ was substituted for the hydroxymethanesulfonic acid and illustrates the lowered conversion rates obtained with H$_2$SO$_4$.

| | Reactants | | | Conditions | | | |
|---|---|---|---|---|---|---|---|
| Example | Acetone Cyanohydrin (mmol) | Hydroxymethane-sulfonic Acid (mmol) | Water (mmol) | Reaction Time (hr) | Temperature (°C.) | Conversion (%) | Selectivity (%) |
| 1 | 100 | 150 | 650 | 2 | 70 | 89 (77) | 35 (32) |
| 2 | 100 | 150 | 650 | 1 | 70 | 65 | 63 |
| | | | | 2 | 70 | 100 | 59 |
| | | | | 3 | 70 | 100 | 50 |
| | | | | 4 | 70 | 100 | 61 |
| 3 | 100 | 150 | 650 | 1 | 70 | 83 (78) | 39 (59) |
| | | | | 3 | 70 | 89 (85) | 52 (62) |
| 4 | 100 | 300 | 1300 | 2 | 70 | (100) | 59 (100) |
| | | | | 3 | 80 | (100) | 93 (100) |
| 5 | 100 | 150(H$_2$SO$_4$) | 650 | 2 | 70 | 4 (12) | (100) |

We claim:

1. A process for producing alpha-hydroxyisobutyric acid which comprises reacting acetone cyanohydrin with alpha-hydroxymethanesulfonic acid and water at a temperature ranging from about 70° C. to about 125° C.

2. The process of claim 1 wherein the temperature ranges from about 75° C. to about 100° C.

3. The process of claim 1 or claim 2 wherein the molar ratio of reactant alpha-hydroxymethanesulfonic acid to reactant acetone cyanohydrin ranges from about 1.5 to about 7 and the molar ratio of water to reactant acetone cyanohydrin ranges from about 5 to about 10.

4. The process of claim 1 wherein the alpha-hydroxymethanesulfonic acid is prepared by reacting formaldehyde, water and sulfur dioxide.

5. The process of claim 5 wherein the alpha-hydroxymethanesulfonic acid is prepared in situ.

* * * * *